(12) United States Patent
Haley

(10) Patent No.: US 7,763,209 B2
(45) Date of Patent: Jul. 27, 2010

(54) SAMPLE PREPARATION DEVICE AND METHOD

(75) Inventor: Cecelia Haley, Northville, MI (US)

(73) Assignee: HandyLab, Inc., Ann Arbor, MI (US)

( * ) Notice: Subject to any disclaimer, the term of this patent is extended or adjusted under 35 U.S.C. 154(b) by 1354 days.

(21) Appl. No.: 11/078,183

(22) Filed: Mar. 11, 2005

(65) Prior Publication Data

US 2005/0214927 A1    Sep. 29, 2005

Related U.S. Application Data

(60) Provisional application No. 60/551,787, filed on Mar. 11, 2004.

(51) Int. Cl.
| | | |
|---|---|---|
| B01L 3/02 | (2006.01) | |
| B01D 21/24 | (2006.01) | |
| F04F 10/00 | (2006.01) | |
| G01N 1/00 | (2006.01) | |
| B01D 37/00 | (2006.01) | |
| B01L 99/00 | (2010.01) | |

(52) U.S. Cl. .......... 422/100; 422/101; 422/103; 210/117; 210/767; 137/140; 73/61.68

(58) Field of Classification Search .......... 422/101, 422/103, 100; 210/117, 767; 137/140; 73/61.68
See application file for complete search history.

(56) References Cited

U.S. PATENT DOCUMENTS

| | | | | |
|---|---|---|---|---|
| 4,018,089 A | * | 4/1977 | Dzula et al. | 73/863.58 |
| 4,038,192 A | * | 7/1977 | Serur | 210/321.72 |
| 4,212,744 A | * | 7/1980 | Oota | 210/321.64 |
| 4,800,022 A | * | 1/1989 | Leonard | 210/636 |
| 5,601,727 A | * | 2/1997 | Bormann et al. | 210/767 |
| 5,674,394 A | * | 10/1997 | Whitmore | 210/321.8 |
| 6,010,627 A | * | 1/2000 | Hood, III | 210/321.6 |
| 6,156,199 A | * | 12/2000 | Zuk, Jr. | 210/321.84 |
| 6,398,956 B1 | * | 6/2002 | Coville et al. | 210/321.75 |

* cited by examiner

*Primary Examiner*—Lore Jarrett
(74) *Attorney, Agent, or Firm*—Knobbe Martens Olson & Bear LLP

(57) ABSTRACT

A sample preparation device for reducing a concentration of one or more concomitant components of a sample and/or increasing a concentration of one or more desired sample components is described.

20 Claims, 1 Drawing Sheet

SAMPLE PREPARATION DEVICE AND METHOD

RELATED APPLICATIONS

This application claims the benefit of U.S. provisional application No. 60/551,787, filed Mar. 11, 2004, which application is incorporated herein by reference in its entirety.

FIELD OF THE INVENTION

The invention relates to a sample preparation device as well as to related methods.

BACKGROUND

One of the common difficulties in performing bio-assays is preparing a sample for testing. Raw samples can be obtained from a bodily fluid, bodily waste, or from a swab that is subsequently placed in a buffer solution to release collected cells, DNA, and varying amounts of extraneous matter collected during the swabbing. Current sample preparation techniques can be expensive, labor intensive, time consuming, and can rely heavily on human participation.

Preparation of raw samples for testing typically includes clean up steps, such as forcing the sample through various sizes and types of filters to trap, isolate, screen, or sort out particles that range down to micron and sub-micron sizes. During preparation, samples can be contaminated or otherwise rendered unusable due to handling or simple human error. Proper sample concentration and clean-up reduces clogging especially when used with micro-scale structures.

The recent arrival of point of care devices for use in clinics and doctors' offices has increased the need for a simple, yet robust preparation device that a non-technician can use to perform the critical step of sample preparation at the 'point of care.' This creates an intense need for a device to simplify sample preparation and concentration while maintaining the integrity of the sample.

Current sample preparation and concentration methods usually involve a syringe and a single size filter for each clean up step. Such filters utilize a single direction of fluid flow, and are typically operated using the injection stroke of a syringe to filter out large particles. The sample is filtered through different, successively smaller filters such as by fitting the filters to a different syringe. Each time the filter is changed, technician time increases and the possibility of sample contamination also increases.

SUMMARY

The present invention relates to a sample preparation device as well as to related systems and methods. In general, the result of the sample preparation is to provide a processed sample having a reduced amount of concomitant components relative to an unprocessed sample and/or a processed sample that is enriched in one or more desired sample components relative to an unprocessed sample.

In some embodiments, the invention relates to a device that includes distinct passages having different (e.g., separate) intake/outflow openings and valves. Sample can pass in only one direction along each passage.

In some embodiments, the device is configured to process a sample using both the intake and output motions of a syringe. For example, the intake motion can draw a sample through a first passage of the device and the output motion of the syringe can expel the sample through a second, different passage of the device. This can be performed, for example, without detaching the device from the syringe.

In some embodiments, one or more of the passages can filter the sample and/or one or more of the passages can enrich the sample.

In some embodiments, the device includes an integral pressure device such as a syringe as opposed to being designed for use with a stand-alone pressure device.

The device can include fittings that are compatible with standard syringes, and can be disposed of with standard biomedical waste. The device allows safe injection of samples into micro-fluidic devices without overwhelming such microfluidic devices with excessive pressure.

In some embodiments, a sample processing device includes a body defining a first passage configured to allow passage of fluid in only a first direction with respect to the body and a second passage configured to allow passage of fluid in only a second, different direction with respect to the body. A fluid retention member is disposed along at least one of the first and second passages. The fluid retention member is configured to retain fluid that passes along the first and second passage so that the amount of fluid that exits the passage is less than the amount of fluid that entered the passage.

DETAILED DESCRIPTION

Figure 1:
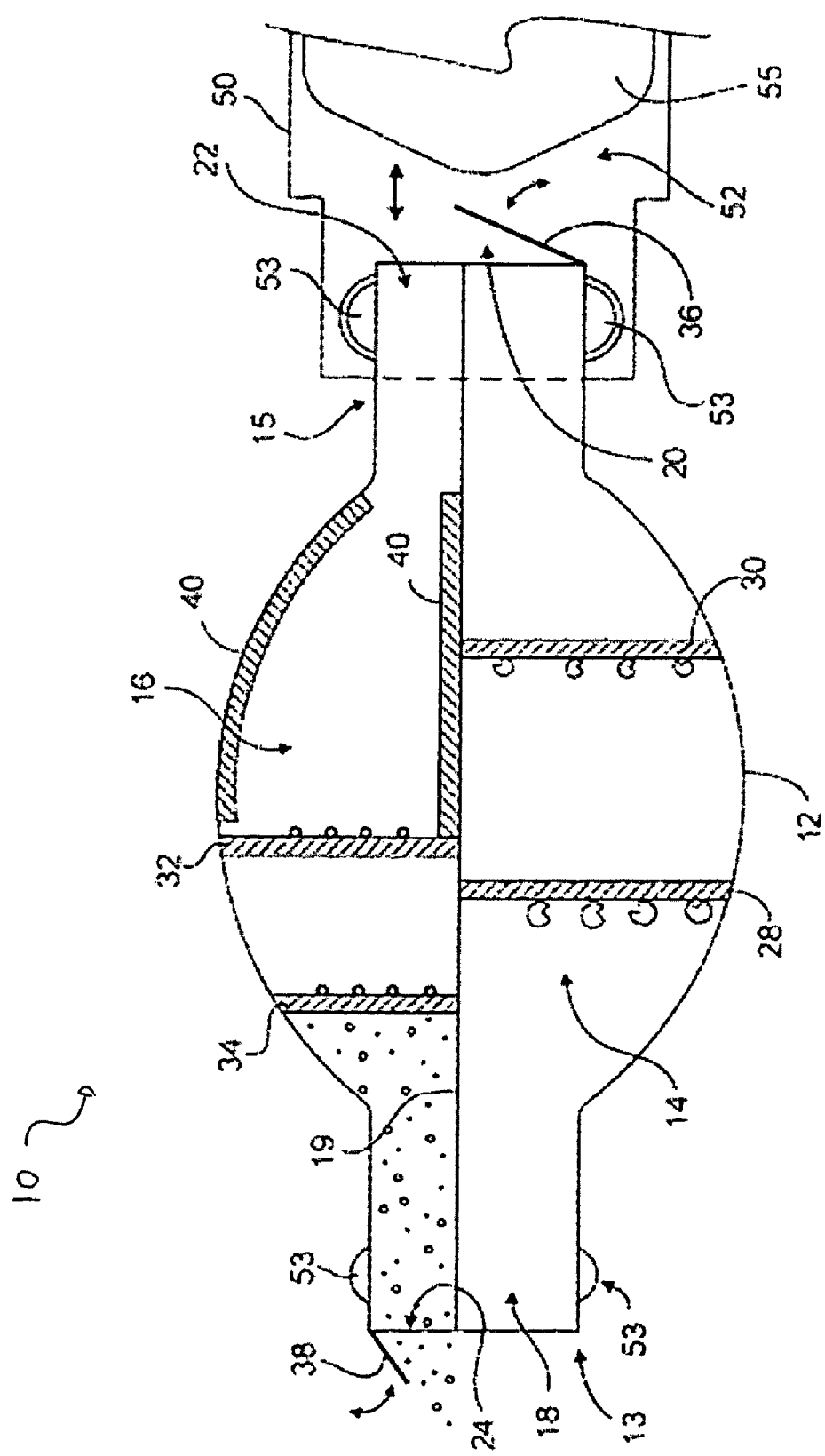
FIG. 1 shows an embodiment of a sample preparation device.

Referring to FIG. 1, a sample preparation device 10 is configured to process a sample including (a) at least one desired sample component, e.g., one or more polynucleotides or other biological material, one or more cells, viruses, or other microorganisms and, typically, (b) one or more concomitant components, e.g., one or more polynucleotides or other biological material, cells, viruses, or other microorganisms, tissue, particulates and the like. The desired and concomitant components of the sample can be entrained in a fluid (e.g., a liquid). Typical samples include blood and samples generated from tissue swabs and other tissue samples such as by combining a tissue or cell sample with buffer. Device 10 processes such samples to provide a processed sample including: (a) a reduced amount (e.g., none) of concomitant components (if present in the original sample) relative to the amount of a desired sample component(s), (b) a processed sample enriched in the desired sample component(s) relative to an amount of fluid entraining the desired sample component, or (c) a processed sample having both of these properties.

Device 10 includes a body 12 defining a first end 13, a second end 15, a first passage 14 and a second passage 16. Body 12 is shown as, bulb shaped but may have other configurations (e.g., cylindrical, rectangular, or onion shaped). First passage 14 has a first opening 18 and a second opening 20. Second passage 16 has a first opening 22 and a second opening 24. In general, first passage 14 provides a passage for the intake of a sample by device 10, whereas the second passage 16 provides a passage for the output of a processed sample by device 10. A wall 19 isolates first and second passages 14, 16 from one another such that desired sample components and, generally, other material cannot pass between the passages except via openings thereof.

First and second ends 13, 15 of device 10 include a fitting 53 (e.g., a Luer loc fitting) so that device 10 can be coupled to other devices (e.g., to a syringe, a source of sample, or to another processing device).

Second opening 20 of first passage 14 includes a valve 36 configured to allow fluid and particles to exit first passage 14 via second opening 20 and to limit or prevent entry of fluid and particles to first passage 14 via second opening 20. Second opening 24 of second passage 16 includes a valve 38 configured to allow fluid to exit second passage 16 via second opening 24 and to limit or prevent entry of fluid and particles to second passage 16 by second opening 24. Valves 36 and 38 are generally one-way valves.

In use, a vacuum source (e.g., a syringe 50) is mated with second opening 20 of first passage 14 and first opening 22 of second passage 16. The first end 18 of first passage 14 and the second opening 24 of the second passage 16 are contacted with a sample (e.g., a sample to be processed). A plunger 55 of syringe 50 is withdrawn to apply a reduced pressure to second opening 20 of first passage 14 and to first opening 22 of second passage 16. Valve 38 at second opening 24 of second passage 16 closes to prevent sample from entering the second passage. Sample is drawn into first passage 14 through first opening 18, drawn along first passage 14, and then withdrawn from first passage 14 through second opening 20 and valve 36. The exiting sample typically enters a reservoir of the vacuum source (e.g., a barrel 52 of syringe 50).

The plunger of syringe 50 is then depressed to apply pressure to sample within barrel 52. Valve 36 closes to prevent material from reentering first passage 14. Sample is pushed into second passage 16 through first opening 22, pushed along second passage 16, and pushed from second opening 24 through valve 38 to exit device 10. Second passage 16 can have smaller dimensions (e.g., a smaller radial cross section) than first passage 14. The smaller cross section can reduce the force required to move material through the second passage.

Sample is typically subjected to at least one processing step (e.g., enrichment of desired sample components and/or concomitant component reduction or removal as by filtration) while traveling through each of the first and second passages.

In embodiments configured to at least reduce the relative amount of concomitant sample components, device 10 can include at least one and optionally a plurality of retention elements configured to retain concomitant components of the sample while allowing passage of desired sample components. For example, retention elements, e.g., filters 28, 30, 32, and 34, can retain particles having a size greater than the size of the desired sample component(s). Filters 28, 30, 32, and 34 may be, for example, a torturous path filter or a screen or mesh type filter. The type of filter in each device depends upon the components of the sample and the filtration requirements. Filters 28, 30, 32, and 34 generally retain particles of decreasing size. First sample passage 14 can have greater dimensions, e.g., a greater radial cross section, than second passage 16 to allow filters disposed along first passage 14 to have a greater surface area than if the passages had the same size cross sections.

It should be noted that filters 28, 30, 32, and 34 may also (or alternatively) be configured as adsorptive filters configured to adsorb and/or bind one of the desired sample component(s) and concomitant sample components to a greater extent than the other. Filters 28, 30, 32, and 34 can be formed of any material compatible with samples to be processed.

In embodiments configured to provide a processed sample enriched in the desired sample component(s) relative to the amount of fluid, device 10 can include a fluid retention member 40 configured to retain fluid of the sample to a greater extent than the one or more desired sample components. For example, retention member 40 can comprise a porous network capable of retaining a given amount of fluid. The porous network can be hydrophilic. The porous network can comprise a ceramic medium, such as moderately or hard fired alumina, or a porous glass medium. Other suitable materials include polymers, e.g., polytetrafluoroethylene or polyethylene, configured as porous networks.

The void volume of the porous medium can be at least 15%, at least 25%, or at least 30% of the porous network. Retention member 40 is generally configured to minimize retention of the desired sample component. For example, the pore size can be selected to be smaller than the size of the desired sample component. Retention member 40 can include a layer, e.g., a coating, configured to minimize association, e.g., adsorption, by the retention member 40 of the desired sample component.

As an alternative to or in combination with a porous network, retention member 40 can comprise an absorptive medium configured to retain water by absorption such as through solvation. Preferred absorptive media comprise a plurality of chemical constituents, e.g., hydroxyl groups, organic acid groups, hydrogen bonding groups, ionic groups, and the like, with which water can associate. Exemplary polymers include acrylates, e.g., sodium polyacrylate, cellulose, e.g., carboxymethylcellulose and hydroxyethylcellulose, and acrylamide polymers. The absorptive medium can comprise a substantial amount of cross linked material.

In some embodiments, device 10 is configured to receive a sample having a liquid volume of at least about 500 microliters (e.g., at least about 1000 microliters, at least about 2000 microliters, at least about 5000 microliters) into opening 18 of first passage 14. In some embodiments, device 10 is configured to receive a sample having a liquid volume of no more than about 750 microliters (e.g., no more than about 1500 microliters, no more than about 2500 microliters, no more than about 10000 microliters) into opening 18 of first passage 14.

In some embodiments, device 10 is configured to provide (e.g., from second opening 24 of second passage 16) a processed sample having a liquid volume of no more than about 90% (e.g., no more than about 80%, no more than about 65%, no more than about 50%, no more than about 25%) of the liquid volume of the sample introduced into opening 18 of first passage 14. At least some (e.g., most or essentially all) of the remaining liquid is retained by one or more retention members of device 10. Because the one or more retention members retain liquid preferentially to the desired sample material, the processed sample can be enriched in the desired sample material by at least about 10% (e.g., at least about 20%, at least about 35%, at least about 50%, at least about 75%, or more) as compared to the sample introduced to first opening 18 of first passage 14.

Device 10 can be formed of material including but not limited to metal, polymer, e.g., plastic, polytetrafluoroethylene, nylon, or any other polymer, co-polymer or synthetic type material that is sufficiently inert with respect to desired sample materials. Components of device 10, e.g., valves and filters as discussed below, can be secured using, e.g., laser or ultrasonic welding, adhesives including epoxies, solder, heat staking, press fitting, and the like.

Other embodiments are within the claims.

What is claimed is:

1. A sample processing device, comprising:
   a body having a first end and a second end;
   a first passage having a first and a second opening and extending between the first and second end;

a second passage having a first and a second opening and extending between the first and second end;

a first valve configured to allow material from a sample to pass only from the first opening of the first passage toward the second opening of the first passage and into a reservoir of a vacuum source;

a second valve configured to allow material from the sample to pass only from the reservoir into the first opening of the second passage toward the second opening of the second passage; and at least one of a liquid retention member or a retention element disposed inside at least one of the first and second passages, wherein the liquid retention member is configured to retain at least a portion of the material from the sample that passes along the passage and the retention element is configured to selectively bind particles of a first type while allowing particles of a second, different type to pass without substantial binding, wherein the first and second passages are arranged and configured so that the vacuum source can be simultaneously coupled to the second opening of the- first passage and the first opening of the second passage, wherein the vacuum source is configured to apply and reduce the pressure in the first and second passages to open and close the first and second valves, and wherein a wall isolates the first and second passages from one another such that material cannot pass between the first and second passages except via the respective first and second openings thereof.

2. The sample processing device of claim 1, wherein the vacuum source is a single syringe.

3. The sample processing device of claim 2, wherein the reservoir is a barrel of the single syringe.

4. The sample processing device of claim 2, wherein the syringe comprises a plunger configured to be withdrawn or depressed.

5. The sample processing device of claim 1, wherein at least one of the first and second passages includes a retention element.

6. The sample processing device of claim 5, wherein the retention element is a filter.

7. The sample processing device of claim 1, wherein at least one of the first and second passages includes a liquid retention member.

8. The sample processing device of claim 7, wherein the liquid retention member is configured to retain at least 30% of liquid that passes through the device.

9. The sample processing device of claim 7, wherein the liquid retention member is a hydrophilic porous network.

10. The sample processing device of claim 1, wherein the first and second passages each include at least one liquid retention member.

11. The sample processing device of claim 1, wherein at least one of the first and second passages includes a liquid retention member and at least one of the first and second passages includes a retention element.

12. The sample processing device of claim 1, wherein the first valve is configured to allow material from the sample to pass only in a first direction from the first opening of the first passage toward the second opening of the first passage and into a reservoir of a vacuum source, and wherein the second valve is configured to allow material from the sample to pass only in a second and opposite direction from the reservoir into the first opening of the second passage toward the second opening of the second passage.

13. A sample processing device comprising:
a first end securable to a source of sample;
a second end securable to a vacuum source;
a first passage and a second passage, extending between the first and second ends, and each having a respective first opening and a respective second opening,
wherein the second opening of the first passage includes a first valve configured to allow one-way passage of a sample from the source along the first passage from the first opening of the first passage toward the second opening of the first passage, wherein the second opening of the second passage includes a second valve configured to allow one-way passage of the sample along the second passage from the first opening of the second passage toward the second opening of the second passage, and wherein a wall isolates the first and second passages from one another such that the sample cannot pass between the first and second passages except via the respective first and second openings thereof.

14. The sample processing device of claim 13, wherein at least one of the first and second passages comprises a liquid retention member configured to reduce an amount of liquid present in the sample relative to an amount of a desired sample component present in the sample.

15. The sample processing device of claim 14, wherein the liquid retention member is configured to retain at least 30% of liquid that passes through the device.

16. The sample processing device of claim 14, wherein the liquid retention member is a hydrophilic porous network.

17. The sample processing device of claim 13, wherein the vacuum source is a single syringe.

18. The sample processing device of claim 17, wherein the reservoir is a barrel of the single syringe.

19. The sample processing device of claim 13, wherein at least one of the first and second passages includes a retention element.

20. The sample processing device of claim 19, wherein the retention element is a filter configured to selectively retain particles of a first size while allowing particles of a second, smaller size to pass therethrough.

* * * * *